Figure 1:
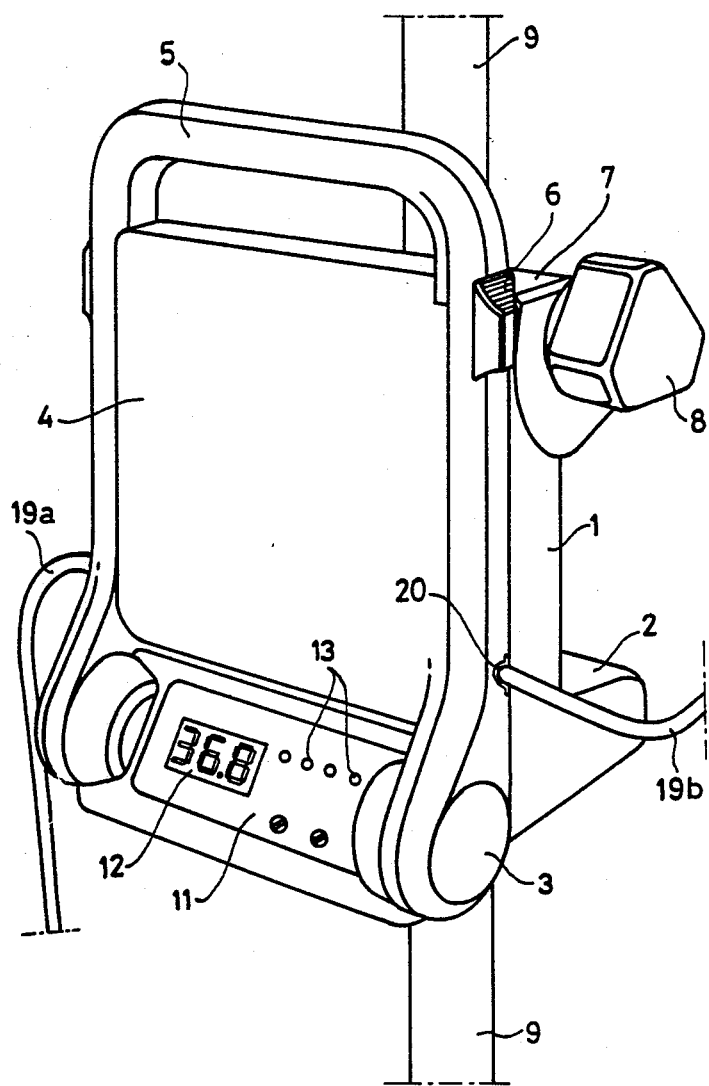

United States Patent [19]

van Leerdam

[11] Patent Number: 4,906,816
[45] Date of Patent: Mar. 6, 1990

[54] BLOOD HEATING APPARATUS FOR HEATING PLASTIC BLOOD SUPPLY POUCHES

[75] Inventor: Johannes M. L. van Leerdam, Berkhout, Netherlands

[73] Assignee: Medistad Holland B.V., Netherlands

[21] Appl. No.: 196,233

[22] Filed: May 20, 1988

[30] Foreign Application Priority Data

May 22, 1987 [NL] Netherlands ............... 8701233

[51] Int. Cl.⁴ .................. H05B 1/02; A61F 7/12
[52] U.S. Cl. ...................... 219/299; 219/301; 219/303; 219/313; 219/330; 604/114
[58] Field of Search ........... 219/299, 301, 302, 303, 219/313, 494, 497, 501, 507, 330, 331; 604/114; 128/400

[56] References Cited

U.S. PATENT DOCUMENTS

| | | | |
|---|---|---|---|
| 3,480,015 | 11/1969 | Gonzalez | 128/276 |
| 3,590,215 | 6/1971 | Anderson et al. | 219/330 |
| 4,314,143 | 2/1982 | Bilstad | 219/497 |
| 4,523,078 | 6/1985 | Lehmann | 219/202 |
| 4,680,445 | 7/1987 | Ogawa | 219/299 |

Primary Examiner—M. H. Paschall
Attorney, Agent, or Firm—Larson and Taylor

[57] ABSTRACT

A blood heating apparatus, comprising a box provided with a hinged door with pins for suspending thereon a plastics pouch having a labyrinth-shaped passage communicating with flexible inlet and outlet tubes, said box and door are provided with temperature-controlled electrical heating assemblies to be contacted with both sides of said pouch and with passages for the tubes of said pouch. The door is hinged at its lower side on a horizontal hinge axis, and is provided with said suspension pins, the inlet and outlet tubes of said pouch communicating with said pouch symmetrically at two opposite sides being mutually aligned, the passages for said tubes in the box and door walls being situated in the vicinity of the hinge axis of said door.

10 Claims, 4 Drawing Sheets

BLOOD HEATING APPARATUS FOR HEATING PLASTIC BLOOD SUPPLY POUCHES

When transfusing blood it is important that the transfused blood will have substantially the normal body temperature. In order to bring the blood arriving from a transfusion pouch, which often has a rather low temperature, on said desired temperature, blood heaters are used which consist of a box provided with a hinged door and with pins for suspending thereon a plastics pouch with a labyrinth-shaped passage formed therein communicating with flexible inlet and outlet tubes for, respectively, the blood to be heated and the heated blood, said box, furthermore, being provided with temperature-controlled electrical heating means to be contacted with both sides of said pouch, and with passages for the tubes of said pouch.

The current apparatus of this kind are generally mounted on a vertical support column on which also the blood supply pouch can be suspended, said apparatus comprising a door with a vertical hinge axis, said supporting pins for the plastics pouch being situated within the box proper, and the inlet and outlet tubes being led through the box wall at the side opposite from the door hinge and at the upper and lower sides respectively of said pouch. Suspending such a plastics pouch in the box and removing it from the box is rather cumbersome since said pins, which are rather short and thin, are not very accessible in said box, and the pouch is to be suspended in a given orientation. This can be objectionable if the outlet tube is to be led towards the opposite side, and arranging and removing the pouch can be more difficult for left-handed people than for right-handed ones.

The invention provides an improvement of such an apparatus which can be operated in a more simple and easy manner, and is, to that end, characterised in that said door is hinged at its lower side on a horizontal hinge axis, means being provided for keeping the opened door in a substantially horizontal position, said door being provided with said suspension pins, the inlet and outlet tubes of said pouch communicating with said pouch symmetrically at two opposite sides and mutually aligned, the passages for said tubes in the box wall being situated in the vicinity of said hinge axis.

The pins provided on the door are, in particular long and relatively thick pins facilitating attaching a pouch and retaining the pouch unambiguously also when closing the door, said pins fitting in adapted recesses in the box.

For improving the safety, the door can be provided with two separately operating latches which are symmetrically arranged near the upper side of the door, which latches can be easily actuated with two hands.

Since the door can be swung forwards into a horizontal position, and, furthermore, is provided with the suspension pins, arranging and removing the plastics pouch is considerably simplified, since, now, said pins are accessible from above and each in the same manner. This is simplified still more as the pouches, as to the connections thereof, are fully symmetrically shaped. A consequence thereof is, moreover, that the position of the inlet and outlet tubes can be adapted to the conditions of use, and that no difference in ease of manipulation for left- and right-handed people exists.

If said heating apparatus are not mounted on a support, they should be adapted to be placed on the ground. In order to ensure a stable position when supported on the ground, it is preferred that the portion serving for accommodating the plastics pouch and proveded with the swing door includes an angle of less than 90° with the bottom portion comprising the electric control and connection parts.

In a preferred embodiment the hinge axis of the swing door is formed by two hinge bearings at the lateral edges of the bottom portion and the extended lateral edges of the door resp., and the intermediate front wall of said bottom portion is constructed as a control and reading panel which is, in particular, inclined under an angle facilitating reading and control.

In particular a handle can be formed integrally with the upper side of said door, allowing to carry said apparatus in a favourable position, and, furthermore, facilitating opening and closing said swing door.

In order to ensure a good temperature control of the blood, in particular irrespective of the inlet velocity of the blood and the orientation of the inlet and outlet tubes in respect of the apparatus, the heating elements can be divided into at least two partial areas with separate electronic heating control means, each being adapted to provide, in the respective area of the pouch, an optimal hest control. Preferably said heating elements are constructed as heating plates with temperature sensors included therein, said plates requiring little space. The control means are, in particular, adapted for quickly warming up the apparatus.

Figure 2:
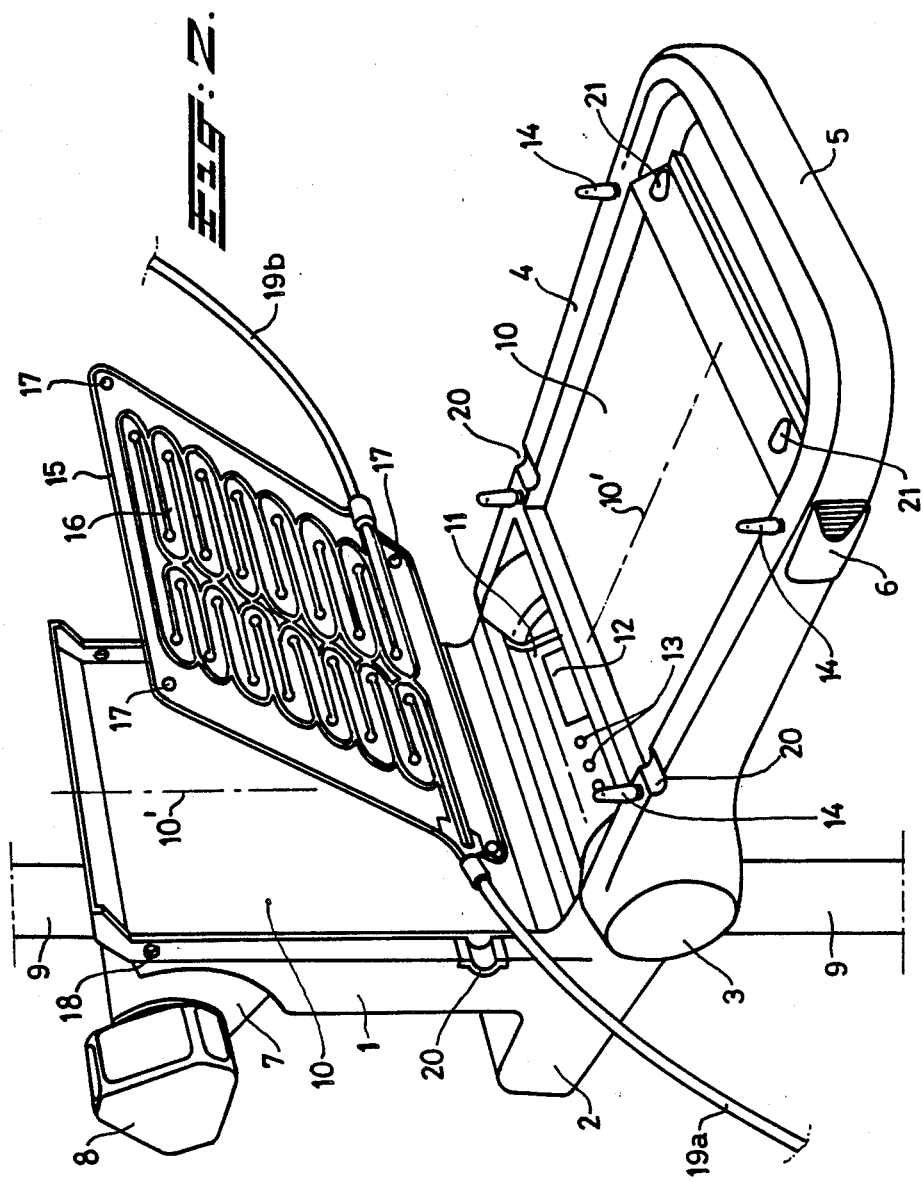
Figure 3:
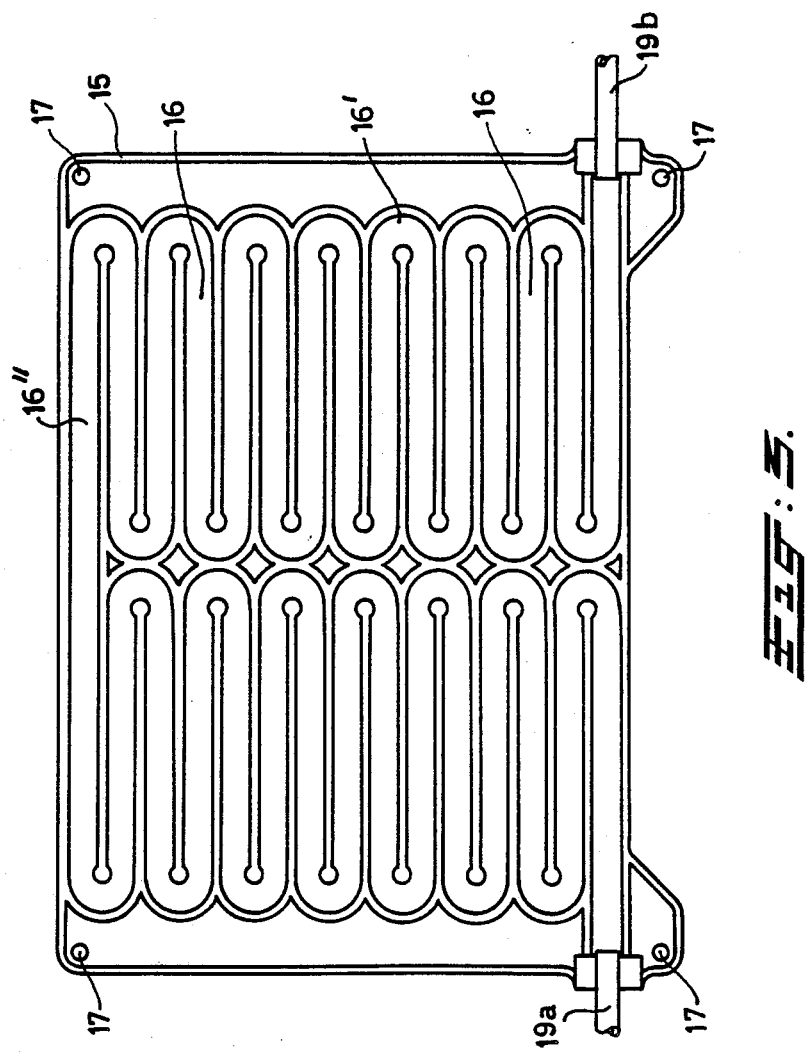

The invention will be elucidated below in more detail by reference to a drawing, showing in:

FIG. 1 a representation in perspective of a preferred embodiment of the apparatus of the invention in the closed condition;

FIG. 2 a simplified representation corresponding with FIG. 1 of this apparatus in the opened condition;

FIG. 3 a front view of a plastics pouch suitable for this apparatus; and

Figure 4:
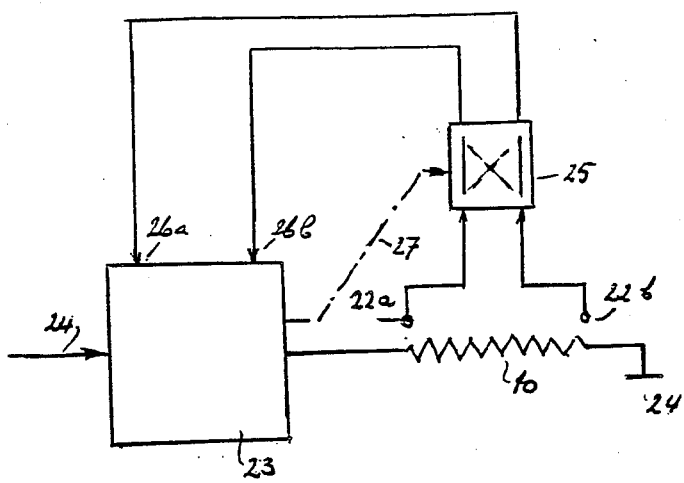
Figure 5:
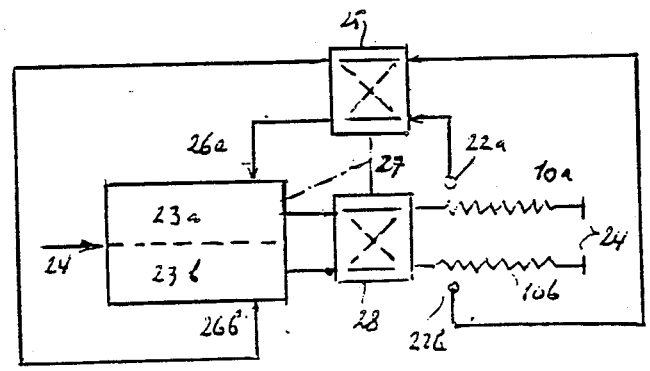

FIGS. 4 and 5 simplified diagrammatic representations of temperature control means for such an apparatus.

The apparatus according to the invention shown in FIGS. 1 and 2 comprises a box 1 with, at its lower side, a rearwardly extending bottom portion 1 and, at the front side of said bottom portion 2, a hinge bearing 3 for the forwardly rotatable swing door 4 with a handle 5 which, at the same time, can be used for carrying the apparatus, and, in its vicinity, at both sides an actuating knob 6 for unlatching the door 4 is arranged. At the rear side of the box 1 a clamp 7 is provided having a tensioning knob 8 for mounting the apparatus on a support column 9.

The box 1 and swing door 4 are provided with electrical heating plates 10 diagrammatically shown in FIG. 2, the front wall of the bottom portion 2 situated between the hinge bearings 3 being formed as a control panel 11 with a temperature indicator 12 and adjusting and/or warning elements 13 for controlling the operation of said heating plates 10.

As apparatus from FIG. 2, the swing door 4 can be swung open towards a substantially horizontal position, the hinge bearings 3 being provided thereto with adapted stops. At the inner side of the swing door 4 four projecting pins 14 are provided serving for fixing thereon a plastics pouch 15 with a labyrinth-shaped passage 16 as shown in FIGS. 2 and 3, said pouch being provided with four holes 17 corresponding with said pins 14.

These pins 17 are so long that the pouch 15 can be easily fixed thereon, and will remain suspended thereon when closing the door. In the edge portion of the box recesses 18 for accommodating said pins are provided. The edge of the pouch 15 is, then, maintained in the correct position in respect of the heating plates 10 between the edges of the box 1 and the door 4.

This pouch 15 comprises two mutually aligned flexible connecting tubes 19a and 19b, each communicating with an extremity of the labyrinth passage 16. This passage 16 comprises, in the case shown in FIG. 3, two adjacent series of passage portions interconnected by bends 16', and with a connecting passage 16" at the side remote from the connection 19. Also other shapes of the passage are possible, provided that the connections 19 are mutually aligned.

If such a plastics pouch 15 is fixed with its holes 17 on the pins 14 of the swing door 4, the tubes 19 will, when closing the swing door 4, land in the corresponding recesses 20 in the lateral walls of the box 1 and the door 4, so as to allow to lead the connecting tubes 19 outwards from the box 1 in a sufficiently sealing manner.

As a consequence of the symmetry of the plastics pouch 15, it is immaterial how this pouch is laid on the pins 14, provided that the connecting tubes 19 will land in the recesses 20. Arranging and removing a pouch 15 is substantially simplified as the pins 14 are completely accessible on the swing door 4 when swung outwards in its horizontal position, and this equally well for left- and right-handed people, and also because of the fact that the pouch is completely symmetrical, it then being immaterial which of the connections 19a and 19b will be used as the inlet or outlet, respectively, so that their position can be adapted to the conditions of use. The connections with the transfusion needle and the blood supply pouch will be realised later by means of the usual couplings.

The bottoms 2' of the bottom portion 2 preferably includes with the rear wall of the box 1 and angle of less than 90°, so that, when the apparatus is put down, the box will have a slight rearward slant, which provides a stable position.

In the apparatus shown two latch knobs 6 are provided, each cooperating with an associated latching lug 21 (FIG. 2). In order to open the door 4, the knobs 6 are to be actuated with both hands (e.g. the thumbs), but, this is very simple because of the symmetrical position thereof. A very safe locking is obtained thereby.

The heating plates 10 are, in particular, provided with printed circuits so that a very small transverse dimension is obtained. Preferably said circuits are divided into two or more partial areas, as diagrammatically shown in FIG. 2 by a central bisecting line 10. These partial areas are separately fed by the electronic control means included in the box portion 3, and heat sensors not shown are present for determining the temperature prevailing in the partial area in question, and to transfer it towards the control means. In this manner an optimal heating can be obtained irrespective of the position of the supply hose, and irrespective of the flow rate of the blood through the pouch 15.

In particular said control means are adapted for a quick warming-up of the apparatus according to a given programmed warming-up function. Moreover the parts 13 can include warning lamps for dangerous conditions (such as a too high blood temperature or an other control disturbance, mains failure or the like).

In FIGS. 4 and 5 two highly simplified diagrams of control means for controlling the temperature of the heating plates 10 are shown.

FIG. 4 shows a single heating element 10 (which, for the rest, consists of two portions situated at both sides of a pouch 15), which element is supplied by means of a control stage 23 with power terminals 24 (one shown as being a ground connection). The temperature sensors 22a and 22b measure the temperature of the pouch 15 at a corresponding extremity thereof. A commutator 25 is adapted to connect these sensors 22 with one of the inputs 26a and 26b resp. of the control stage 23, said inputs influencing the inlet and outlet temperature control respectively. Depending on the orientation of the pouch 15 in the box 1, the commutator is to be set. As indicated by an interrupted line 27 this can also be done automatically, if the stage 23 is adapted to determine which sensor 22 has measured the lowest or highest temperature respectively. A built-in warming-up programme will, then, adjust the warming-up power accordingly, in order to bring the blood at the desired temperature as fast as possible.

FIG. 5 shows a modified diagram for the case of heating elements which are subdivided into two partial areas 10a and 10b, each being connected with an associated portion 23a or 23b of the control stage, which portions are adapted to control the warming-up and outlet temperatures resp., and which, depending on the position of the commutator 25, are each connected with one of the sensors 22. A second commutator 28 is adapted for making a corresponding connection of the elements 10a and 10b. Actuating the commutators 25 and 28 can, again, take place automatically depending on the temperature measured.

It should be noted that these diagrams are highly simplified representations, and that, in particular, the commutators 25 and 28 will, in practice, be incorporated in the control circuitry, the latter being constructed in such a manner that the desired adjustment of the temperature measurement and of the current supply will be brought about automatically.

Sometimes it can be desirable to subdivide the heating elements into three or more partial areas, and then only the outer ones are to be commutated, and the or each intermediate area is to be controlled so that a favourable transition between both other areas will be obtained.

It will be clear, moreover, that said control stage can be constructed in many ways.

In the preceding description only blood heating has been discussed, but it will be clear that the present apparatus can also be used for heating other liquids, e.g. infusion liquids or the like, which are to be administered at a given and substantially constant temperature.

I claim:

1. In blood heating apparatus comprising a box provided with a hinged door and with pins for suspending thereon a plastic pouch with a labyrinth-shaped passage formed therein communicating with flexible inlet and outlet tubes for, respectively, the blood to be heated and the heated blood, said box and door being provided with temperature-controlled electrical heating means for contacting both sides of a pouch suspended in said box to provide heating of said pouch, and with passages for the tubes of said pouch, the improvement wherein said door is hinged at the lower side thereof on a hinge axis which, in the orientation of the apparatus during use thereof extends horizontally, means being provided for keeping the opened door in a substantially horizontal position, said door being provided with said pouch suspending pins, the inlet and outlet tubes of said pouch communicating with said pouch symmetrically at two opposite sides and being mutually aligned, and the passages for said tubes in the box and door walls being situated in the vicinity of said hinge axis of said door.

2. The apparatus of claim 1, wherein said pins are of sufficient length that a pouch suspended thereby is held securely in place even during closing of the door, said pins fitting in adapted recesses in the box.

3. The apparatus of claim 1, wherein the door is provided with two separately operating latches which are symmetrically arranged near the upper side of the door.

4. The apparatus of claim 1, wherein the box includes a bottom on which the box can be supported, the plane of forming an angle of less than 90° with the plane of the door when closed.

5. The apparatus of claim 1, wherein the hinge axis of the door is formed by two hinge bearings disposed in a bottom portion of the box and in extended lateral edges of the door, respectively, the intermediate front wall of said bottom portion being constructed as a control and reading panel which is inclined rearwardly at an angle so as to facilitate reading and control.

6. The apparatus of claim 1, wherein a handle is provided at the upper side of said door, the handle serving as a carrying handle.

7. The apparatus of claim 1, wherein the heating means comprise heating plates with printed circuits with temperature sensors included therein.

8. The apparatus of claim 1, wherein said heating means includes heating elements, control means, and two temperature sensors for measuring the temperature of the pouch near one of the tube connections, said sensors being connected with a respective input of said control means, one of said sensors measuring the inlet temperature, and the other one measuring the outlet temperature, said control means being adapted to control the electric power supplied to said heating elements in such a manner that the outlet blood flow has the desired temperature, said apparatus further comprising a commutator means for, depending on the connection mode of said tubes, enabling one of said sensors to be connected as the input sensor and the other one as the output sensor.

9. The apparatus of claim 8, in which the heating elements are subdivided into at least two partial areas with separate heating control, one of said areas serving for quickly warming-up the supplied blood, and the other area for maintaining the desired outlet temperature thereof, said apparatus further comprising a further commutator by means for enabling said mutually identical partial areas to be connected in turn as a warming-up and a temperature maintaining element respectively.

10. The apparatus of claim 8, whereby at least one of the commutator means can be actuated by means of an element for determining which sensor is measuring the lowest temperature.

* * * * *